United States Patent [19]

Leniger-Follert

[11] Patent Number: 5,008,269

[45] Date of Patent: Apr. 16, 1991

[54] METHOD FOR TREATING CIRCULATORY VESSEL OCCLUSION

[76] Inventor: Elfriede Leniger-Follert, Sprinkstück 3, D-5800 Hagen, Fed. Rep. of Germany

[21] Appl. No.: 342,756

[22] Filed: Apr. 25, 1989

Related U.S. Application Data

[63] Continuation-in-part of Ser. No. 124,938, Sep. 8, 1987, abandoned.

[51] Int. Cl.⁵ .............................................. A01N 43/40
[52] U.S. Cl. ..................................... 514/277; 514/836
[58] Field of Search ................................. 514/277, 836

Primary Examiner—Stanley J. Friedman
Assistant Examiner—Greg Hook
Attorney, Agent, or Firm—Felfe & Lynch

[57] ABSTRACT

This invention concerns a method for using an ion exchange resin as a pharmaceutical for treating circulatory disturbances especially to aid in combating circulatory vessel constrictions or occlusions. An example of the method uses Resonium A resin.

1 Claim, No Drawings

METHOD FOR TREATING CIRCULATORY VESSEL OCCLUSION

This application is a continuation-in-part of U.S. Ser. No. 124,938, filed Sept. 8, 1987, now abandoned.

DESCRIPTION

The invention relates to a pharmaceutical for combating circulatory disturbances, and a method using ion-exchange resins.

Circulatory disturbances may have different causes. They can be caused, for instance, purely mechanically by an arterial occlusion, for instance, a thrombus or embolus, or an angiostenosis in the case of changes of the vascular walls, or by a cardiogenic and cardiovascular decrease in the blood pressure below a critical lower perfusion pressure. Moreover, circulatory disturbances may be caused by a disordered blood composition. The circulation in an organ or in the entire organism may be only diminished or totally interrupted, compared to the normal state. As a consequence of the circulatory disturbance there results an oxygen- and substance deficiency, a diminished removal of the final products of metabolism and a damage of the cell membranes in the affected organ or in the entire organism.

Depending on the degree of the decrease in blood supply, this has serious consequences in the affected regions and thus results in critical syndromes which may even lead to death.

Physiopathologically speaking, in the case of a disturbance first calcium ions flow out of the extracellular space and into the cell, and in counter-direction, potassium ions flow out of the cells and into the extracellular space. Moreover, an increased lactate formation results in an intra- and extracellular acidosis. First of all, the increase in the potassium concentration in the extracellular space first in the range of 3 to 20 mmol per litre results in a dilatation of the arterial blood vessels through a hyperpolarisation of the smooth vascular muscle cell membrane. Above 20 mmol per liter, a further increase in the $K^+$ concentration in the extracellular space results in a narrowing of the blood vessels, caused by a $K^+$ depolarisation of the smooth vascular muscle cell membrane. The $K^+$ concentration can increase to a maximum of 100 mmol per litre and may lead to a total occlusion of the arterial blood vessels. An increase in the extracellular $K^+$ concentration, which has a narrowing effect on the vessels, can also be effected by a release of potassium ions from erythrocytes after a haemorrhage into the tissue, for instance, after a subarachnoid haemorrhage in the case of cerebral aneurysms.

The narrowing of the vessels caused by the increased potassium concentration in the extracellular space has very serious consequences for the affected organs or tissues. It is the actual reason why the circulation cannot be put in action again after a primary disturbance. This leads to a final destruction of cells and tissue debris, thus resulting in syndromes, especially in the cerebral and coronary region, which may even lead to death.

Cerebral and coronary circulatory disturbances are widespread in the population. Thus, there is a need for providing a pharmaceutical for the treatment of these diseases.

Therefore, it was the object of the invention to provide a pharmaceutical suitable for the treatment of circulatory disturbances, in particular, in the cerebral and coronary region.

This object is attained by a pharmaceutical for combating circulatory disturbances, which is characterized in that it contains as active substance at least one substance trapping potassium ions at physiological pH values, optionally together with conventional physiological additives, solvents and/or diluents.

Surprisingly, it has been found that circulatory disturbances can be treated successfully with a composition capable of trapping potassium ions in the extracellular region. With the help of this new pharmaceutical the narrowing of the arterial blood vessels in the organs which is caused by an increase in the $K^+$ concentration between 20 and 100 mmol is offset and the vessels are dilatated so that the blood can flow again.

For combating circulatory disturbances the pharmaceutical contains a substance trapping potassium ions. This active substance possesses the K-ion-trapping properties both at normal and physiopathological pH values. For this purpose there is used a compound capable of selectively complexing the potassium ions, whereby $Na^+$, $Ca^{++}$, and $Mg^{++}$ are not complexed. Preferably, the compound should be water-soluble since it is supplied to the blood. Moreover, the compound should not be too strongly fat-soluble so that it cannot penetrate through the cell membrane. This substance, of course, must not be toxic to man. Furthermore, this substance must not be mutagenic or teratogenic.

Preferably, the potassium-ion-trapping substance is applied together with conventional additives, solvents and/or diluents. These agents are known to the skilled worker.

In particular an ion exchange resin such as Resonium A can be used.

The potassium-ion-trapping substance preferably is a compound having the general formula

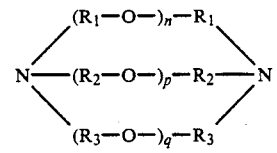

wherein $R_1$, $R_2$ and $R_3$ independently are an alkyl group having 1 to 4 C-atoms and n, p and q independently are an integer from 1 to 5.

These compounds which are referred to as cryptates are extremely well suited for the selective complexation of potassium ions. They are soluble in water and non-toxic. Particularly preferably, those compounds are used in which $R_1$, $R_2$ and $R_3$ are a $C_2$-alkyl group, and n, p and q are 2.

It is preferred to render the cryptates even more water-soluble by introducing hydrophilic substituents.

It is an advantage of this preferably applied compound that in the complexing of potassium the pH value is slightly increased. In the case of the insufficient supply caused by the circulatory disturbance the pH value shifts to the acidic range. Therefore, it is particularly advantageous that this acidotic shifting which may lead to the cells dying off is prevented by the composition according to the invention.

A further preferred substance trapping potassium ions is a crown ether. A preferred crown ether is a compound having the general formula

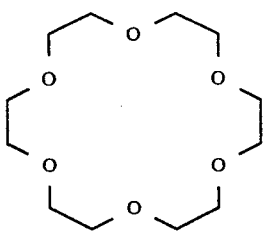

wherein the C-atoms 1, 2 and 7, 8 may be part of a cyclohexyl- or benzyl group.

The compounds referred to as crown ethers are also very suitable for the selective complexation of potassium ions. Preferably, those crown ethers are used, in the case of which the two rings are substituted with hydrophilic groups. A particularly preferred compound is the compound referred to as [18--crown-6 showing no rings.

Furthermore, common additives may be added to the pharmaceutical, whereby, in particular, physiologically suitable buffer substances can be used in this connection. As buffer substances, in particular, tris buffer, bicarbonate or phosphate buffer are used. In a preferred embodiment a thrombolytic additive is added to the pharmaceutical. This is appropriate, in particular, if the circulatory disturbance to be treated is caused by the occlusion of a vessel, for instance, through a thrombus in the case of an infarct. Furthermore, anti-oedematic agents may be added to the pharmaceutical.

In particular, in the case of a disturbed coronary flow it is furthermore preferred to add to the pharmaceutical a compound acting as a calcium antagonist.

The pharmaceutical composition according to the invention is suitable for the treatment of all kinds of circulatory disturbances. It can be used for the treatment of circulatory disturbance of any organ and with respect to the whole organism. The composition is suitable for generalized and local circulatory disturbances. It is particularly preferred in the treatment of cerebral and coronary circulatory disturbances. A preferred kind of application is also the treatment of cerebral circulatory disturbances in new-born children.

The composition may be applied systemically. Due to its good water-solubility the composition can be administered in the form of injections and infusions, whereby injection is preferably effected intra-arterially. However, it is also possible to administer the composition intravenously. As an infusion the pharmaceutical is contained preferably in a rheologically active infusion to haemodilute the blood. Moreover, the composition can also be administered orally in the form of drops of tablets. To treat disturbed circulation of individual organs, it is further preferred to inject the composition directly into the affected organ. In the case of a cerebral infarct, for example, the composition is injected directly into a cerebral artery and in the case of a cardiac infarction directly into the heart. In particular, if the heart is concerned, it is also preferred to instal a catheter and to introduce the composition via this catheter.

Furthermore, the composition may also be applied locally to the affected organ directly from outside. After a haemorrhage in the region of the pial cerebral artery, for example, the composition can be applied through a drilled hole or during the neurosurgical operation on the brian to eliminate the localized or generalized spasms by the $K^+$ release after a haemorrhage.

The dosage of the pharmaceutical composition is dependent on the kind and location of the circulatory disturbance. The composition can be dosed exactly depending on the potassium concentration at the location of the circulatory disturbance.

Preferably, the pharmaceutical composition is applied at such concentration that the potassium ion concentration is adjusted to a range of from 3 to 20 mmol, especially preferred from 3 to 10 mmol.

The pharmaceutical composition according to the invention can be used to treat circulatory disturbances and occlusion of vessels. The composition leads to the vessel constriction being eliminated and the ischemia being overcome. Thus, it is possible surprisingly to prevent or at least diminish damages caused by ischemia.

The invention shall be further illustrated by the following examples:

EXAMPLE 1

The effect of (2,2,2)-cryptate on the $K^+$ concentration in rat brain was examined. The $K^+$ activity of the cerebral cortex was measured on a narcotised rat with a $K^+$ sensitive valinomycin surface electrode. The physiological parameters were in normal range. The $K^+$ basic concentration on the cerebral cortex was 4.5 mmol/l and was constant. Then about 100 μl of a 100 mmol KCl solution were applied dropwise to the whole opened surface of the brian. The $K^+$ activity of the brain increased to 34 mmol/l. Dropwise application of 100 mmol (2,2,2)-cryptate dissolved in physiological sodium chloride solution made the $K^+$ activity decrease immediately. After 2 minutes approximately the total potassium applied was trapped and the $K^+$ basic value of 4.5 mmol/l restituted.

After 4 ½ minutes the $K^+$ value was 4.2 mmol. Repeated local supply of KCl from outside onto the cerebral cortex at the same amount and concentration as before made the $K^+$ value rise to only 5.6 mmol/l. Repeated addition of cryptate led to a decrease of the $K^+$ activity in the tissue to 4.4 mmol/l.

The $K^+$ electrode was removed from the tissue and the surface of the brain rinsed several times with warm physiological NaCl solution and NaCl was sucked off. Then the $K^+$ electrode was fixed again and the $K^+$ value of 4.5 mmol/l measured. Repeated application of 100 mmol KCl solution now led to a $K^+$ increase in the tissue to 20 mmol/l. By adding (2,2,2)-cryptate the $K^+$ concentration decreased to 4.5 mmol/l within 2 ½ minutes.

EXAMPLE 2

The effect of (2,2,2)-cryptate on the cerebral blood flow of the anaesthetized rat was examined. The changes in cerebral blood flow in the microcirculation range were measured continuously and qualitatively by means of the local hydrogen clearance according to the process by Stosseck and Lübbers modified according to LenigerFollert and Lübbers using a $H_2/pH_2$ surface element according to Leniger-Follert and Lübbers or Barthelt and Leniger-Follert, resp..

First, the blood flow at normal physiological control parameters and a normal $K^+$ value of the brain and steady state conditions was monitored continuously over about 10 minutes. During this period the blood flow remained utterly constant and was in the normal range.

Then 30 μl of a 100 mmol KCl solution were applied to the brain surface directly at the measuring point. The blood flow took a two-phase course. First, it increased immediately and decreased after about 10 seconds and fell far below the basic value. Circulation became defective (ischemia). After another 40 seconds about 40 μl of (2,2,2)-cryptate were added from outside to the brain tissue. Within a few seconds the blood flow immediately increased strongly and after about 1 minute was above the basic range.

EXAMPLE 3

The effect of (2,2,2)-cryptate on the $K^+$ concentration was tested in one unbuffered and one buffered solution. The $K^+$ concentration in the solution was measured by means of a $K^+$-sensitive valinomycin surface electrode.

(a) The effect of (2,2,2)-cryptate on the potassium activity and potassium concentration range, resp., was examined in the unbuffered system at different basic pH values.

The $K^+$ ions were present as dissolved KCl in physiological (0.9%) NaCl. The pH value of the solution was adjusted by means of a concentrated NaOH. As a basic solution 4 ml of a 100 mM KCl dissolved in 0.9% NaCl were used. To each solution 1 ml 500 mM (2,2,2)-cryptate were added which was dissolved in 100 mM KCl as well as 0.9% NaCl to avoid a dilution effect. After the mixing of the solutions 5 ml of a solution were obtained having the following concentration: 100 mM KCl, 100 mM (2,2,2)-cryptate, 0.9% NaCl. In the case of theoretical 100% complexation of the potassium ions thus the whole free potassium can be complexed.

The solutions used had the following pH values: pH 7, 8, 10. In the case of all three solutions more than 80% complexation of the potassium occurred. After the addition of the cryptate, however, the pH value was in the alkaline range at 9. Only in the case of the basic solution having pH 10 the pH value changed only slightly (cf. Table 1).

TABLE 1

| pH value of the basic solution | $K^+$ concentr. of the basic solut. | $K^+$ concentr. after addition of cryp | ph value of mixture |
|---|---|---|---|
| 10 | 100 mM | 19 | 9.8 |
| 8 | 100 mM | 16 | 8.9 |
| 7 | 100 mM | 16 | 8.9 |

As can be clearly seen from the table, the basic concentration of 100 mM decreases to values of below 20 mM in the case of all three pH stages after the addition of an equivalent amount of cryptate.

(b) Due to the above-described pH shift a second test was carried out, wherein the system was buffered and less strong a concentration of basic substances was used.

The solutions (both the KCl basic solution as well as the cryptate solution) were buffered with 0.1 M phosphate buffer ($Na_2HPO_4$ and $NaH_2PO_4$) to pH 7.

As a basic solution the following mixtures were used: 4 ml 50 mM KCl; 0.9% NaCl; 0.1 phosphate buffer pH 7; 1 ml 250 mM (2,2,2)-cryptate; 50 mM KCl; 0.9% NaCl; 0.1 M phosphate buffer.

The addition of the complexation agent led to a decrease in the $K^+$ activity of more than 50%, whereby the pH shifted only slightly to the alkaline range. The pH value changed by 0.4 units to pH 7.4.

TABLE 2

| pH value of basic solut. | $K^+$ concentr. of basic solution | $K^+$ concentr. after addition of cryp. | pH of the mixture |
|---|---|---|---|
| 7.0 | 50 mM | 22 | 7.4 |

EXAMPLE 4

Description of an experiment and results with Resonium A

The effect of the ion exchanger Resonium A (poly(styrene, divinylbenzene)sulfonic acid, sodium salt) on the diameters of the arterial and arteriolar vessels on the exposed brain surface of the anaesthetized rat was examined. The physiological blood parameters such as blood pressure, blood gases and the pH, as well as the ionic concentrations of the blood were all within normal ranges. The vessel reactions were observed by means of an appropriate direct light microscope and a section of the brain surface with the vessels was photographed prior to and after the application of the corresponding substance by a camera positioned on the microscope.

Three vessels were marked in the observation section of the microscope by means of a microscope marking in the control state under starting conditions and photographed. Subsequently, a 1-molar KCl solution was dropped with a pipette on the brain surface and the reaction of the marked vessels was observed. Within seconds, the diameters of the vessels narrowed. After about 2 minutes, the vessels were photographed again. Subsequently, Resonium A was applied in an emulsion onto the brain surface and the vessels were photographed again after 2 minutes and 10 minutes after the application of Resonium. After completing the experimens, the diameters of the three marked vessels were measured, with the developed photographs being enlarged appropriately. The diameter of the three vessels under control conditions, in each case, was put 100% and the percentage change of the diameters of the vessels after the KCl and the Resonium application was determined (Table 3).

TABLE 3

| | diameter |
|---|---|
| vessel 1 | |
| control | 100% |
| KCl | 68.4% |
| Res. (2 min.) | 89.5 |
| Res. (10 min.) | 94.7 |
| vessel 2 | |
| control | 100 |
| KCl | 86.6 |
| Res. (2 min.) | 113.3 |
| Res. (10 min.) | 106.7 |
| vessel 3 | |
| control | 100 |
| KCl | 82.6 |
| Res. (2 min.) | 87.0 |
| Res. (10 min.) | 118.3 |

From the percentage changes of the diameters of the vessels, the changes of flow were calculated according to Hagen-Poiseuille's law. The initial flow was put 100% in each case, in the control state (Table 4).

TABLE 4

|  | flow in % |
|---|---|
| vessel 1 | |
| control | 100 |
| KCl | 21.4 |
| Res. (2 min.) | 64.2 |
| Res. (10 min.) | 80.4 |
| vessel 2 | |
| control | 100 |
| KCl | 56.2 |
| Res. (2 min.) | 164.8 |
| Res. (10 min.) | 129.6 |
| vessel 2 | |
| control | 100 |
| KCl | 46.6 |
| Res. (2 min.) | 57.3 |
| Res. (10 min.) | 118.3 |

Evaluation: As is shown by the test results, decreases in the blood supply caused by potassium ions are cancelled by the applied ion exchanger.

These results support the action of ion exchangers used for the trapping of potassium and the effects achieved thereby on the arterial vessels of the brain. They show the constriction of these vessels in the case of KCl being administered and the cancellation of this constrictive effect and even a dilatation of the vessels, compared to the basic value prior to the addition of KCl, in the case of the ion exchanger treatment.

The ion exchange resin used, i.e. Resonium A, is polystyrene sulfonic acid salt cross-linked with divinylbenzene sulfonic acid. Its theoretic exchange capacity is 135 mg potassium/g resin. Under practical conditions, however, only about ⅓ of this theoretical capacity is occupied by potassium ions.

This resin is known as a pharmaceutical used in the case of potassium intoxications, in particular, hyperkalaemia in the case of dialysis patients. The present invention thus represents a new use. The resin as well as analogous resins of other manufacturers is normally used in the form of the sodium or calcium salt.

It will be understood that the specification and examples are illustrative but not limitative of the present invention and that other embodiments within the spirit and scope of the invention will suggest themselves to those skilled in the art.

I claim:

1. A method for treating a circulatory disturbance and occlusion of vessels in a mammal comprising administering to said mammal the ion-exchange resin Resonium A in an amount sufficient to trap up to 135 mg of potassium per gram of resin.

* * * * *

UNITED STATES PATENT AND TRADEMARK OFFICE
CERTIFICATE OF CORRECTION

PATENT NO. : 5,008,269
DATED : April 25, 1991
INVENTOR(S) : Elfriede Leniger- Follert It is certified that error appears in the above-indentified patent and that said Letters Patent is hereby corrected as shown below:

On the title page, Item [22] change filing date form "April 25, 1989" to -- April 24, 1989--.

Column 1, line 22, change "As" to -- As --.

Column 3, line 20, change "[18. -crown-6" to -- [18]--

Item [56] insert -- priority documents German application No. 3543974 December 12, 1985 and PCT Application PCT/EP 86/00695 December 2, 1986.--

Signed and Sealed this

Twenty-sixth Day of October, 1993

Attest:

BRUCE LEHMAN

Attesting Officer

Commissioner of Patents and Trademarks